United States Patent [19]

Ali

[11] 4,385,047
[45] May 24, 1983

[54] ANTIALLERGIC IMIDODISULFAMIDES

[75] Inventor: Fadia E. Ali, Cherry Hill, N.J.

[73] Assignee: SmithKline Beckman Corporation, Philadelphia, Pa.

[21] Appl. No.: 222,478

[22] Filed: Jan. 5, 1981

[51] Int. Cl.$^3$ .................... A61K 31/47; C07D 401/12
[52] U.S. Cl. ...................................... 424/43; 424/258; 546/139; 546/140; 546/146; 564/82
[58] Field of Search ................... 546/140; 424/258, 43

[56] References Cited

U.S. PATENT DOCUMENTS

| Re. 24,763 | 1/1960 | Neesby | 546/140 |
| 3,062,813 | 11/1962 | Scott | 546/140 |
| 3,882,148 | 5/1975 | Augstein et al. | 424/283 |
| 4,252,818 | 2/1981 | Rokach et al. | 424/283 |
| 4,296,129 | 10/1981 | Kadin et al. | 424/309 |

OTHER PUBLICATIONS

Kalaus et al., "Chemical Abstracts", vol. 72, 1970, Col. 100456h.

Primary Examiner—Donald G. Daus
Assistant Examiner—James H. Turnipseed
Attorney, Agent, or Firm—Joseph F. DiPrima; Richard D. Foggio; Alan D. Lourie

[57] ABSTRACT

Imidodisulfamide derivatives useful in the treatment of allergic conditions are prepared by reaction of an appropriately substituted tetrahydroisoquinoline and bis-(chlorosulfonyl)imide in the presence of a non-nucleophilic organic base. Pharmaceutical compositions and methods of alleviating the symptoms of an allergic response are also disclosed.

14 Claims, No Drawings

ANTIALLERGIC IMIDODISULFAMIDES

This invention relates to novel imidodisulfamides which are useful as end-organ antagonists of slow reacting substance of anaphylaxis, pharmaceutical compositions and methods of alleviating the symptoms of an allergic response. The substance, SRS-A, has been suggested to be an important mediator of anaphylaxis in human asthma. By antagonizing the effects of this or other pharmacologically active mediators at the end-organ, bronchial smooth muscle, the compounds of this invention are valuable in the treatment of allergic diseases such as asthma.

The imidodisulfamide compounds of this invention are represented by the following general structural formula (I):

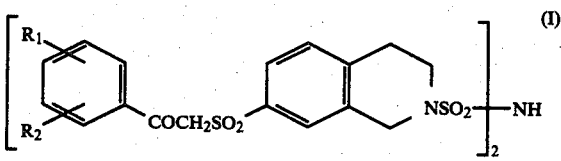

wherein $R_1$ is hydrogen, bromo, chloro, nitro, methyl, trifluoromethyl or methoxy and $R_2$ is hydrogen, chloro or methyl with the proviso that when $R_2$ is chloro, $R_1$ is chloro, methyl or trifluoromethyl; and alkali metal salts of said compounds.

Particular compounds of the instant invention are compounds of the formula (I) wherein:

(a) $R_2$ is hydrogen and $R_1$ is hydrogen; 3- or 4-bromo; 2-, 3- or 4-chloro; 3-nitro; 3- or 4-trifluoromethyl; or 4-methoxy;
(b) $R_2$ is 3-chloro and $R_1$ is 4-chloro or 4-methyl;
(c) $R_2$ is 4-chloro and $R_1$ is 3-trifluoromethyl; and
(d) $R_2$ is 3-methyl and $R_1$ is 4-methyl.

Specific compounds of the instant invention are the compounds of the formula (I) wherein $R_2$ is hydrogen and $R_1$ is 4-bromo or 4-chloro.

The compounds of the formula (I) are conveniently prepared as shown in the following scheme:

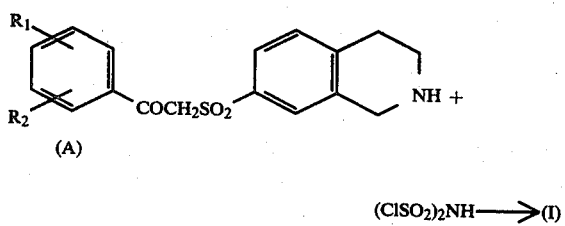

in which $R_1$ and $R_2$ are as described above. Thus, the appropriately substituted tetrahydroisoquinoline is reacted with bis(chlorosulfonyl)imide in the presence of a non-nucleophilic organic base.

Examples of such non-nucleophilic organic bases include tertiary alkylamines, such as triethylamine, tertiary alkylaryl amines, such as N,N-dimethylaniline and aromatic amines, such as pyridine.

The reaction is carried out in an inert polar organic solvent. The selection of a particular solvent is not critical provided that the solvent is substantially inert to the reagents and product. Illustrative of such a solvent is acetonitrile.

The reaction is usually carried out at moderate to low temperatures. For example, the reagents are usually mixed at temperatures of 0° C. or less and the reaction is allowed to warm gradually to ambient temperature.

The reaction time is dependent on inter alia the particular starting materials, solvent and reaction temperature. Generally, the reaction will be allowed to proceed for at least 12 hours.

The reaction product can be isolated by standard methods, for example, addition of dilute mineral acid e.g. hydrochloric acid, to the reaction mixture affords the compounds of formula (I) as the "free acid".

Alkali metal salts of the compounds of the formula (I), for example, the sodium or potassium salts, are obtainable by treatment of the compounds with the appropriate metal alkoxide, for example methoxide, in an alkanol solvent such as methanol; by treatment of the compounds with an alkali metal hydride, such as sodium hydride or potassium hydride, in a polar nonprotic solvent, such as tetrahydrofuran, or dimethoxyethane; or by treatment of the compounds with a cationic exchange resin, such as a sulfonic acid resin in the sodium form.

The starting appropriately substituted tetrahydroisoquinolines of the formula (A) are conveniently prepared by standard reactions well known in the chemical arts as shown below:

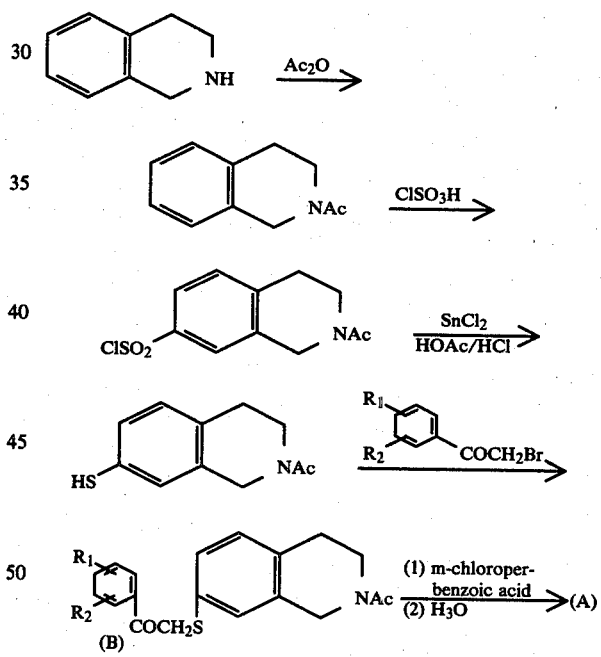

2-Acetyl-7-chlorosulfonyl-1,2,3,4-tetrahydroisoquinoline, which is prepared by acylating and then chlorosulfonating 1,2,3,4-tetrahydroisoquinoline, is reduced to 2-acetal-7-mercapto-1,2,3,4-tetrahydroisoquinoline employing stannous chloride in acetic acid-hydrochloric acid mixture. The 2-acetyl-7-mercapto-1,2,3,4-tetrahydroisoquinoline is then condensed with the appropriately substituted α-bromo acetophenone to afford 2-acetyl-7-benzoylmethylthio-1,2,3,4-tetrahydroisoquinoline (B) which is then oxidized with m-chloroperbenzoic acid and hydrolyzed to yield the desired 7-benzoylmethylsulfonyl-1,2,3,4-tetrahydroisoquinoline (A). Bis(chlorosulfonyl)imide is prepared from chlorosulfonic acid and chlorosulfonylisocyanate.

The SRS-A antagonist activity of the compounds of this invention is measured by the ability of the active medicament to inhibit SRS-A induced contraction of guinea pig ileum. In this test system, sections of ileum are resected from guinea pigs and placed in 5 ml. tissue baths containing a modified Tyrode's solution. One end of the tissue is fixed to a glass tissue holder, the other is connected to a force-displacement transducer and the tissue is placed under a tension of 500 mg. Isometric tissue contractions are recorded on a six channel polygraph. Baths are constantly aerated with 95% $O_2$–5% $CO_2$. After a 20 minute stabilization period a concentration of the appropriate agonist which provides a contraction height of 60–80% of the maximum obtainable to that agonist (as determined from full sequential concentration—response curves in separate experiments) is added to the tissue bath and the response recorded. The procedure is repeated until reproducible responses are obtained. For most agonists, two applications in rapid succession, followed 15 minutes later by a third, is sufficient to establish reproducibility. Experimental tissues are incubated with the selected concentration of the test compounds for 15 minutes. Experimental and control tissues are subjected to 5 bath changes during the incubation interval. Changes in bath fluid during the incubation period are helpful in insuring the reproducibility of tissue responses to the agonist. The same concentration of the agonist is reapplied in the presence of the test compound and the response registered and compared with controls. Percent inhibition produced by the test compound is calculated by subtracting the mean percentage change in control tissue from the mean percentage change in tissues exposed to the test compound. Additional compounds are then evaluated as long as the tissue remains reproducibly responsive to the agonist. Six tissues obtained from 6 animals are used simultaneously—3 controls and 3 experimental.

The compounds of this invention tested at concentrations of from $5 \times 10^{-5}$ M to $1 \times 10^{-6}$ M produce marked antagonism of partially purified slow reacting substance of anaphylaxis obtained from guinea pig lung. The agonist is employed at a concentration of 40 µg/ml.

At a compound concentration of $5 \times 10^{-6}$ M, N,N'-bis[7-(4-chlorobenzoylmethylsulfonyl)-1,2,3,4-tetrahydroisoquinolyl]disulfonylimide exhibited 60 percent antagonism.

The specificity of the antagonist activity of the compounds of this invention is demonstrated by relatively low levels of antagonism toward agonists such as potassium chloride, serotonin, histamine and the prostaglandins $F_{2\alpha}$ and $E_2$.

Pharmaceutical compositions of the present invention comprise a pharmaceutical carrier or diluent and an amount of a compound of the formula (I) or an alkali metal salt thereof sufficient to produce the alleviation of the symptoms of asthma and other allergic diseases.

When the pharmaceutical composition is employed in the form of a solution or suspension, examples of appropriate pharmaceutical carriers or diluents include: for aqueous systems, water; for non-aqueous systems, ethanol, glycerin, propylene glycol, corn oil, cottonseed oil, peanut oil sesame oil, liquid parafins and mixtures thereof with water; for solid systems, lactose, kaolin and mannitol; and for aerosol systems, dichlorodifluoromethane, chlorotrifluoro ethane and compressed carbon dioxide. Also, in addition to the pharmaceutical carrier or diluent, the instant compositions may include other ingredients such as, stabilizers, antioxidants, preservatives, lubricants, suspending agents, viscosity modifiers and the like, provided that the additional ingredients do not have a detrimental effect on the therapeutic action of the instant compositions.

The nature of the composition and the pharmaceutical carrier or diluent will of course depend upon the intended route of administration, i.e. parenterally or by inhalation.

In general, particularly for the prophylactic treatment of asthma, the compositions will be in a form suitable for administration by inhalation. Thus the compositions will comprise a suspension or solution of the active ingredient in water for administration by means of a conventional nebulizer. Alternatively the compositions will comprise a suspension or solution of the active ingredient in a conventional liquified propellant or compressed gas to be administered from a pressurized aerosol container. The compositions may also comprise the solid active ingredient dilute with a solid diluent for administration from a powder inhalation device. In the above compositions, the amount of carrier or diluent will vary but preferably will be the major proportion of a suspension or solution of the active ingredient. When the diluent is a solid it may be present in less, equal or greater amounts than the solid active ingredient.

For parenteral administration the pharmaceutical composition will be in the form of a sterile injectable liquid such as an ampul or an aqueous or nonaqueous liquid suspension.

Usually a compound of formula I is administered to an animal or human subject in a composition comprising an amount sufficient to produce an alleviation of the symptoms of an allergic response. When employed in this manner, the dosage of the composition is such that from 0.5 mg. to 500 mg. of active ingredient are administered at each administration. For convenience equal doses will be administered 1 to 4 times daily with the daily dosage regimen being selected from about 0.5 mg. to about 2000 mg.

The pharmaceutical preparations thus described are made following the conventional techniques of the pharmaceutical chemist as appropriate to the desired end product.

Included within the scope of this invention is the method of alleviating the symptoms of an allergic response resulting from a mediator release which comprises administering to an animal or human subject a therapeutically effective amount for producing said alleviation of a compound of formula I, preferably in the form of a pharmaceutical composition. The administration may be carried out in dosage units at suitable intervals or in single doses as needed. Usually the method of this invention will be practiced when relief of allergic symptoms is specifically required, however, the method is also usefully carried out as continuous or prophylactic treatment. It is within the skill of the art to determine by routine experimentation the effective dosage to be administered from the dose range set forth above, taking into consideration such factors as the degree of severity of the allergic condition being treated, and so forth.

The following examples illustrate the preparation of compounds of formula I and their incorporation into pharmaceutical compositions and as such are not to be considered as limiting the invention set forth in the claims appended hereto.

EXAMPLE 1

PREPARATION OF BIS(CHLOROSULFONYL)IMIDE

A mixture of 166 g. (1.42 mole) of chlorosulfonic acid and 202 g. (1.42 mole) of chlorosulfonylisocyanate was heated under reflux (110° C.) in an oil bath until the evolution of carbon dioxide ceased. The crude product was distilled in vacuo to yield bis(chlorosulfonyl)imide, b.p., (1.5 mm.) 100° C., which is used as described hereinafter.

EXAMPLE 2

PREPARATION OF N,N'BIS[7-(4-CHLOROBENZOYLMETHYLSULFONYL)-1,2,3,4-TETRAHYDROISOQUINOLYL]-DISULFONYLIMIDE (COMPOUND 1)

To 0.42 g. (1.95 mmol.) bis(chlorosulfonyl)imide in 20 ml. dry acetonitrile at −40° C. was added dropwise 0.59 g. (5.85 mmol.) dry triethylamine. The reaction mixture was warmed to 0° C. and 1.50 g. (3.89 mmol.) 7-(4-chlorobenzoylmethylsulfonyl)-1,2,3,4-tetrahydroisoquinoline in 0.39 g. (3.89 mmol.) triethylamine, 10 ml. acetonitrile and 10 ml. methylene chloride was added slowly. The resultant mixture was stirred at ambient temperature for about 16 hours. The reaction mixture was filtered and the filtrate concentrated at reduced pressure to afford a crude product. The crude product was partitioned between ethyl acetate and dilute hydrochloric acid. The ethyl acetate fraction was washed with water, dried over anhydrous sodium sulfate and filtered. To the filtrate was added slowly n-hexane until the solution became turbid. Upon standing, white crystals, with a melting point of about 124° C., with decomposition were obtained.

| Analysis | C | H | N | S |
|---|---|---|---|---|
| Calculated | 48.57 | 3.72 | 5.00 | 15.25 |
| Found | 48.32 | 3.79 | 4.69 | 15.04 |

Similarly, following the above procedure, the appropriately substituted tetrahydroisoquinoline may be reacted with bis(chlorosulfonyl)imide to afford the compounds of formula (I) as listed in the following table:

| Compound Number | $R_1$ | $R_2$ |
|---|---|---|
| 2 | H | H |
| 3 | 4-Br | H |
| 4 | 3-NO$_2$ | H |
| 5 | 3-CF$_3$ | H |
| 6 | 4-OCH$_3$ | H |
| 7 | 4-Cl | 3-Cl |
| 8 | 4-CH$_3$ | 3-Cl |
| 9 | 3-CF$_3$ | 4-Cl |
| 10 | 4-CH$_3$ | 3-CH$_3$ |

EXAMPLE 3

PREPARATION OF THE SODIUM SALT OF COMPOUND 1

A solution of N,N'-bis[7-(4-chlorobenzoylmethylsulfonyl)-1,2,3,4-tetrahydroisoquinolyl]disulfonylimide in methanol is passed through an ion exchange column (IR 120-sulfonic acid type in the sodium form) and the column eluted with methanol. The eluant is concentrated to near dryness and the resultant material is triturated with diethyl ether which after filtration under nitrogen affords the desired salt.

Similarly, alkali metal salts of the compounds of the present invention may be prepared.

EXAMPLE 4

As a specific embodiment of a composition of this invention an active ingredient, such as N,N'-bis[7-(4-chlorobenzoylmethylsulfonyl)-1,2,3,4-tetrahydroisoquinolyl]disulfonylimide, is dissolved in sterile water at a concentration of 0.5% and aerosolized from a nebulizer operating at an air flow adjusted to deliver the desired aerosolized weight of drug.

What is claimed is:

1. A compound of the formula (I):

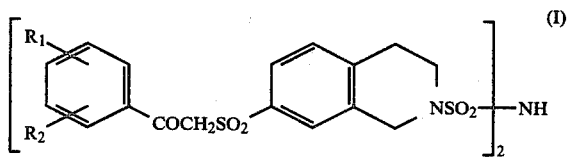

wherein $R_1$ is hydrogen, bromo, chloro, nitro, methyl, trifluoromethyl or methoxy and $R_2$ is hydrogen, chloro or methyl with the proviso that when $R_2$ is chloro, $R_1$ is chloro, methyl or trifluoromethyl; or an alkali metal salt of said compound.

2. A compound according to claim 1 wherein $R_1$ is hydrogen; 3- or 4-bromo; 2-, 3- or 4-chloro; 3-nitro; 3- or 4-trifluoromethyl; or 4-methoxy and $R_2$ is hydrogen or an alkali metal salt of said compound.

3. A compound according to claim 1 wherein $R_1$ is 4-chloro or 4-methyl and $R_2$ is 3-chloro or an alkali metal salt of said compound.

4. A compound according to claim 1 wherein $R_1$ is 3-trifluoromethyl and $R_2$ is 4-chloro or an alkali metal salt of said compound.

5. A compound according to claim 1 wherein $R_1$ is 4-methyl and $R_2$ is 3-methyl or an alkali metal salt of said compound.

6. A compound according to claim 1 which is N,N'-bis[7-(4-chlorobenzoylmethylsulfonyl)-1,2,3,4-tetrahydroisoquinoyl]disulfonylimide or an alkali metal salt of said compound.

7. A pharmaceutical composition of inhibiting the symptoms of asthma comprising a pharmaceutical carrier or diluent and an amount sufficient to produce said inhibition of a compound of claim 1.

8. A pharmaceutical composition according to claim 7 in a form suitable for administration by inhalation.

9. A pharmaceutical composition according to claim 7 comprising a solution or suspension of the active ingredient in sterile water.

10. A pharmaceutical composition according to claim 7 in the form of an aerosol formulation.

11. A pharmaceutical composition according to claim 7 in which the pharmaceutical carrier or diluent is a solid.

12. A method of alleviating the symptoms of asthma which comprises administering to a subject in need of said alleviating a therapeutically effective amount for producing said alleviation of a compound of claim 1.

13. The method according to claim 12 in which the active ingredient is administered in a daily dosage regimen of from about 0.5 mg. to about 2000 mg.

14. A method of antagonizing the effects of SRS-A on bronchial smooth muscle which comprises administering to a subject in need of said antagonism an amount sufficient to produce said antagonism of a compound of claim 1.

* * * * *